United States Patent
Wilson et al.

(10) Patent No.: US 8,855,761 B2
(45) Date of Patent: Oct. 7, 2014

(54) METHOD AND SYSTEM FOR TEMPERATURE ANALYSIS TO PROVIDE AN EARLY MARKER OF CONGESTIVE HEART FAILURE PROGRESS THAT PRECEDES A PATIENT'S SYMPTOMS

(75) Inventors: James W. Wilson, Houston, TX (US); James J. Ferguson, New York, TX (US); Casey D. Cox, Tyler, TX (US)

(73) Assignee: Texas Heart Institute, Houston, TX (US)

(*) Notice: Subject to any disclaimer, the term of this patent is extended or adjusted under 35 U.S.C. 154(b) by 877 days.

(21) Appl. No.: 12/500,990

(22) Filed: Jul. 10, 2009

(65) Prior Publication Data

US 2010/0010552 A1  Jan. 14, 2010

Related U.S. Application Data

(60) Provisional application No. 61/079,589, filed on Jul. 10, 2008.

(51) Int. Cl.
| | |
|---|---|
| *A61N 1/365* | (2006.01) |
| *A61B 5/01* | (2006.01) |
| *A61B 5/00* | (2006.01) |
| *G06F 19/00* | (2011.01) |

(52) U.S. Cl.
CPC .............. *A61B 5/01* (2013.01); *A61B 5/7275* (2013.01); *A61B 5/7257* (2013.01); *A61B 5/726* (2013.01); *A61N 1/3655* (2013.01); *G06F 19/3406* (2013.01)
USPC .................... 607/6; 600/549; 607/21

(58) Field of Classification Search
CPC ................... A61B 5/01; A61B 5/7257
USPC ........................................ 607/6, 21
See application file for complete search history.

(56) References Cited

U.S. PATENT DOCUMENTS

| | | | |
|---|---|---|---|
| 4,685,470 A | 8/1987 | Sekii et al. |
| 4,726,383 A | 2/1988 | Cook et al. |
| 4,741,343 A | 5/1988 | Bowman et al. |
| 4,936,304 A | 6/1990 | Kresh et al. |
| 5,080,106 A | 1/1992 | Sekii et al. |
| 5,462,524 A | 10/1995 | Powell et al. |
| 5,596,995 A | 1/1997 | Sherman et al. |
| 5,620,002 A | 4/1997 | Hughes |
| 5,720,293 A | 2/1998 | Quinn et al. |

(Continued)

OTHER PUBLICATIONS

PCT Written Opinion and Search Report for International Application No. PCT/US2009/050260 Dated Feb. 17, 2010, 10 pages.

*Primary Examiner* — Carl H Layno
*Assistant Examiner* — Jennifer Ghand
(74) *Attorney, Agent, or Firm* — Conley Rose, P.C.

(57) ABSTRACT

The temperature of a patient is a significant predictor of death in heart failure patients. Temperature provides a window into the physiology of the patient's underlying condition and may be used as an early marker for CHF exacerbations. The patient's temperature is taken to form a time series of temperature values. In accordance with some embodiments, the time series of temperature values is converted to the frequency domain by, for example, a discrete Fourier Transform. The frequency domain representation then is analyzed for a marker indicative of the worsening condition of the patient. In accordance with other embodiments, the patient's time series of temperature values is analyzed for a marker using, for example, Cosinor analysis. In yet other embodiments, both the time and frequency domain temperature data is analyzed for markers of the patient's worsening medical condition.

23 Claims, 4 Drawing Sheets

(56) References Cited

U.S. PATENT DOCUMENTS

| | | |
|---|---|---|
| 5,871,449 A | 2/1999 | Brown |
| 6,115,628 A | 9/2000 | Stadler et al. |
| 6,277,082 B1 | 8/2001 | Gambale |
| 6,454,707 B1 | 9/2002 | Casscells, III et al. |
| 6,514,214 B2 | 2/2003 | Kokate et al. |
| 6,752,765 B1 | 6/2004 | Jensen et al. |
| 6,754,516 B2 | 6/2004 | Mannheimer |
| 6,821,249 B2 | 11/2004 | Casscells, III et al. |
| 7,037,273 B2 | 5/2006 | Zhu et al. |
| 7,127,291 B2 | 10/2006 | Zhu et al. |
| 2003/0092975 A1 | 5/2003 | Casscells et al. |
| 2005/0004476 A1* | 1/2005 | Payvar et al. .............. 600/481 |
| 2006/0063982 A1 | 3/2006 | Sullivan et al. |
| 2007/0032734 A1 | 2/2007 | Najafi et al. |

\* cited by examiner

METHOD AND SYSTEM FOR TEMPERATURE ANALYSIS TO PROVIDE AN EARLY MARKER OF CONGESTIVE HEART FAILURE PROGRESS THAT PRECEDES A PATIENT'S SYMPTOMS

CROSS-REFERENCE TO RELATED APPLICATIONS

This application claims the benefit under 35 U.S.C. §119(e) of U.S. Provisional Patent Application No. 61/079,589 entitled, "Method And System For Temperature Analysis To Provide An Early Marker Of Congestive Heart Failure Progress That Precedes A Patient's Symptoms", filed Jul. 10, 2008, the disclosure of which is hereby incorporated herein by reference in its entirety.

BACKGROUND

Physiologic markers indicating the progression of a disease are crucial to the proper modulation of a patient's treatment. Doctors use such markers both as a predictor of future disease course and as a feedback mechanism for optimizing treatment. Unfortunately, many such markers are cost prohibitive and/or are not amenable to repetitive or continuous use in patients away from a medical setting such as a hospital. Doctors often are forced to treat patients based only on symptoms presented at the time of patient-physician interaction. However many predictive symptoms only occur in the later stages of a disease and/or can be subjective in nature. Therefore, the progression of a patient's true condition and a systematic objective prediction of the future disease course frequently remain largely unknown. Early markers that precede the appearance of late-stage symptoms are needed. The earlier a doctor is aware of a patient's condition, the earlier he/she can intervene, possibly slowing or reversing the progression of the disease.

For example, congestive heart failure (CHF) is a chronic and progressive condition. Optimal management of patients with CHF requires close monitoring because CHF patient's clinical status can deteriorate rapidly and suddenly. Therefore, there is continuing need and interest in developing better methods and devices to manage CHF and other chronic diseases.

SUMMARY

The temperature of a patient is a significant predictor of death in heart failure patients. Temperature provides a window into the physiology of the patient's underlying condition and may be used as an early marker for CHF exacerbations. The patient's temperature is taken to form a time series of temperature values. In accordance with some embodiments, the time series of temperature values is converted to the frequency domain by, for example, a discrete Fourier Transform. The frequency domain representation then is analyzed for a marker indicative of the worsening condition of the patient. In accordance with other embodiments, the patient's time series of temperature values is analyzed for a marker using, for example, Cosinor analysis. In yet other embodiments, both the time and frequency domain temperature data is analyzed for markers of the patient's worsening medical condition.

In some embodiments, a method of predicting worsening of a patient's medical condition is described. The method comprises obtaining time domain temperature data (TDTD) pertaining to a patient; converting the TDTD to a frequency domain representation (FDR); and determining a marker indicative of the worsening medical condition by analyzing the FDR or by analyzing the TDTD or by analyzing both. The technique utilized to analyze the TDTD comprises at least one of Cosinor analysis, approximate entropy, tempogram, day-night mean temperature difference, body temperature daily range, interdaily stability, and time-lag embedding.

In some other embodiments, a system for predicting worsening of a patient's medical condition is disclosed. Such a system comprises a processor that receives time domain temperature data (TDTD) pertaining to a patient, converts the TDTD to a frequency domain representation (FDR), and determines a marker indicative of the worsening medical condition of the patient by analyzing the FDR or by analyzing TDTD or by analyzing both. The technique utilized to analyze the TDTD comprises at least one of Cosinor analysis, approximate entropy, tempogram, day-night mean temperature difference, body temperature daily range, interdaily stability, and time-lag embedding. In some cases, such a system further comprises a therapy delivery unit (TDU) that delivers therapy to the patient upon determining the marker indicative of the worsening medical condition of the patient.

In yet other embodiments, a computer-readable storage medium (CRSM) is presented. The CRSM contains software that, when executed by a processor, causes the processor to receive time domain temperature data (TDTD) pertaining to a patient and convert the TDTD to a frequency domain representation (FDR). Furthermore, the processor determines a marker indicative of the worsening medical condition of the patient by analyzing the FDR or by analyzing TDTD or by analyzing both. The technique utilized to analyze the TDTD comprises at least one of Cosinor analysis, approximate entropy, tempogram, day-night mean temperature difference, body temperature daily range, interdaily stability, and time-lag embedding.

In certain embodiments, an implantable medical device is described. The medical device comprises a pacemaker or a defibrillator including an electrical pulse generator and a processor. The processor receives time domain temperature data (TDTD) pertaining to a patient, performs Cosinor analysis on the TDTD, and determines a marker indicative of the worsening medical condition of the patient upon detecting a change in at least one of the mesor, amplitude, and acrophase of the Cosinor analysis of the TDTD. The electrical pulse generator is configured to generate an electrical stimulation signal upon determination of the marker.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques illustrated below, including the exemplary designs and implementations illustrated and described herein, but may be modified within the scope of the appended claims along with their full scope of equivalents.

Overview

The temperature of a patient is a significant predictor of death in heart failure patients. Temperature provides a window into the physiology of the patient's underlying condition and may be used as an early marker for CHF exacerbations. In an embodiment of the invention, a method is disclosed to detect an early marker indicative of the worsening of a patient's medical condition. In some cases, the patient's medical condition is heart failure, such as congestive heart failure (CHF). In some cases, the patient's medical condition is coronary artery disease. Generally speaking, the disclosed method applies to a chronic progressive disease of a patient. In other embodiments of the invention, a device is disclosed that is configured to detect an early marker indicative of the worsening of a patient's medical condition.

The patient's temperature is taken to form a time series of temperature values. In accordance with some embodiments, the time series of temperature values is converted to the frequency domain by, for example, a discrete Fourier Transform. The frequency domain representation then is analyzed for a marker indicative of the worsening condition of the patient. In accordance with other embodiments, the patient's time series of temperature values is analyzed for a marker using, for example, Cosinor analysis. In yet other embodiments, both the time and frequency domain temperature data is analyzed for markers of the patient's worsening medical condition.

Figure 1:
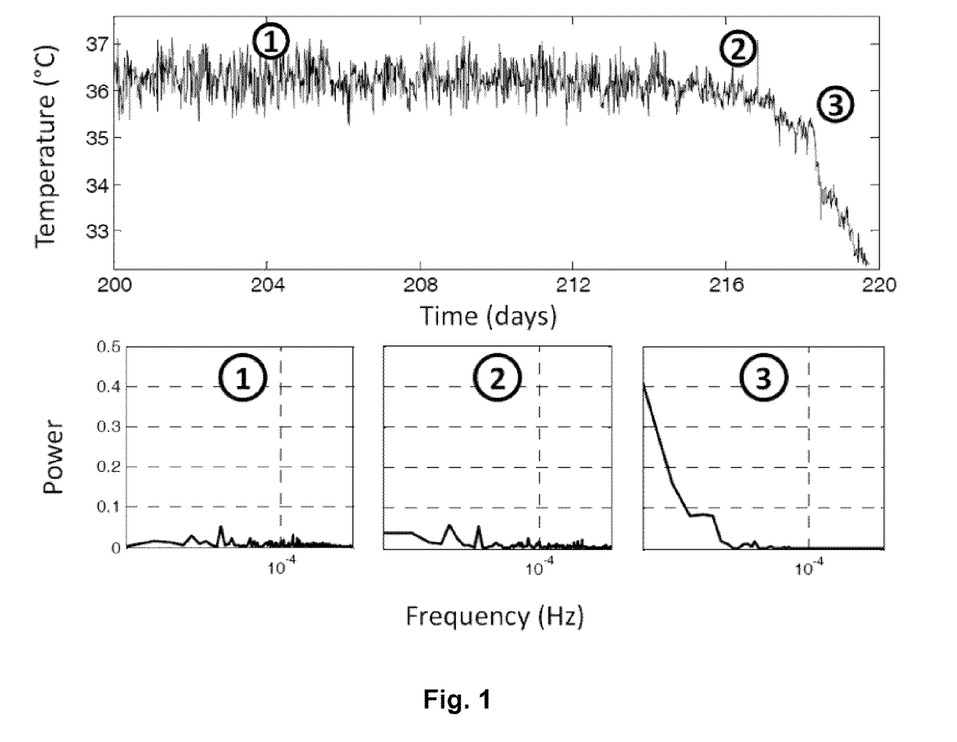
FIG. 1 illustrates that a marker indicative of the worsening medical condition of a patient is detected when an increase occurs in the harmonics of the frequency domain representation (FDR) of the patient's temperature data at frequencies lower than the patient's circadian frequency.

By way of example, as shown in FIG. 1 (top panel), the temperature of a patient has been recorded for 20 days (day 200 to day 220) prior to the death of the patient. The patient's time domain temperature data (TDTD) at time points 1, 2, and 3 of three 6-day periods have been converted to frequency domain representation (FDR) as shown in the bottom panel of FIG. 1. (1, 2, and 3 corresponding to top panel). Corresponding to the temperature decrease at time point 3, an increase is observed (bottom panel, time point 3), in the harmonics of the FDR at low frequencies ($\leq 10^{-5}$ Hz). This is a marker indicative of the worsening medical condition of the patient.

Figure 2:
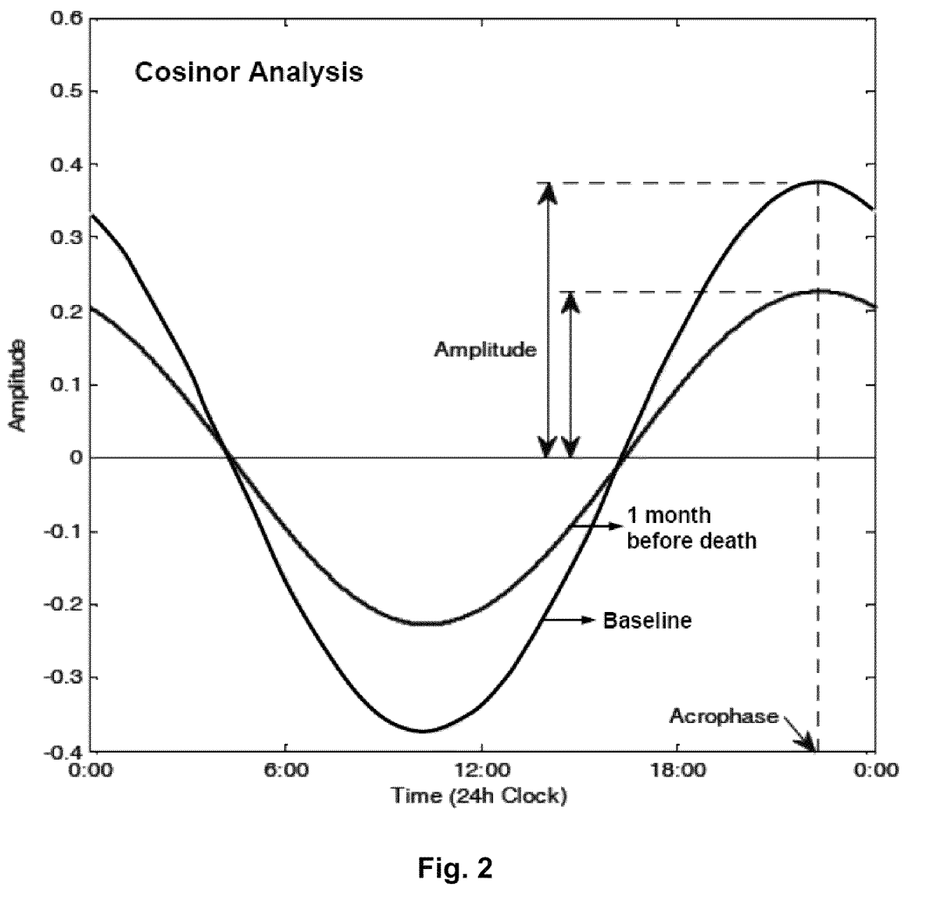
FIG. 2 illustrates that a marker indicative of the worsening medical condition of a patient is determined when a change occurs in the amplitude of the Cosinor analysis of the patient's temperature data.

As shown in FIG. 2, Cosinor analysis is performed using a patient's TDTD to compare the baseline 4-week temperature circadian rhythm ("Baseline") with the 4-week temperature circadian rhythm before death ("1 month before death"). A decrease in the amplitude of the patient's temperature circadian rhythm is observed, shown by Cosinor analysis of the TDTD of the patient. Decrease in amplitude is a marker indicative of the worsening medical condition of the patient. The details of Cosinor analysis and other techniques are described herein below.

Method of Predicting

In accordance with at least one embodiment, a method of predicting worsening of a patient's medical condition comprises obtaining time domain temperature data (TDTD) pertaining to the patient and converting the TDTD to a frequency domain representation (FDR). The method further comprises determining a marker indicative of the worsening medical condition by analyzing the FDR or by analyzing the TDTD or by analyzing both.

The TDTD comprises any suitable temperature parameter. For example, the TDTD is a time series of temperature data taken by a Foley™ catheter or a rectal probe. Other examples of TDTD include core body temperature, tympanic cavity temperature, oral cavity temperature, rectal cavity temperature, axilla temperature, bladder temperature, esophagus temperature, trachea temperature, an airway temperature, and the big toe temperature. In some embodiments, a combination of at least two temperature parameters is utilized.

In some cases, the TDTD is obtained by acquiring temperature values from at least one temperature sensor, such as a thermometer, a Foley™ catheter with a thermistor, or a Swan-Ganz™ catheter. Alternatively, the TDTD is obtained by reading temperature values from storage. Additionally, the TDTD can be obtained by manual input of the measurements of the patient's temperature performed by, for example, the patient or a healthcare provider.

The rate at which the TDTD is sampled may be adjusted according to the practical constraints for implementation. For automated temperature acquisition, the sampling rate may be, for example, once every 15 minutes, once an hour, or once every few hours, depending on factors such as memory capacity and battery power of the temperature acquisition device. For manual temperature acquisition, the sampling rate needs to be as low as possible for convenience and patient compliance. The limit of the lowest sampling rate is dictated by the Nyquist theorem—if a function contains no frequencies greater than or equal to B hertz, this function is determined by giving its ordinates at a series of points spaced 1/(2 B) seconds apart. Since the highest frequency of interest is the circadian frequency (1 cycle per day), the minimal sampling frequency is greater than 2 measurements per day. On the other hand, the advantage of a higher sampling rate is greater certainty.

The TDTD is converted to FDR by a suitable mathematical operation, such as, Fourier transform, wavelet transform, or Chirplet transform. The data window for such conversion is the length of time domain data to be converted to the FDR at a single sampling. The width of the data window sets the limit of the lowest frequency that is detected. For example, a data window of 6 days sets the lowest frequency detected to be 1.9 µHz, i.e., 1 cycle every 6 days. The data window is therefore adjusted to include detection of lower frequencies in the FDR.

In accordance with some embodiments, the TDTD is analyzed by performing at least one of Cosinor analysis, approximate entropy, tempogram, day-night mean temperature difference, body temperature daily range, interdaily stability, and time-lag embedding.

Cosinor analysis uses the least-squares method to fit a cosine wave to a time series data, for example TDTD that demonstrate predictable rhythms, to calculate mesor, amplitude and acrophase from equation $f(t) = M + A \cos((\omega t + \phi))$, where M is the mean value, or mesor; A is the maximum amplitude, or amplitude; $\phi$ is half the peak-to-peak distance, or acrophase; $\omega$ is the angular frequency and t is time. The time series data used for Cosinor analysis may be an unequally spaced time series. In accordance with various embodiments, the angular frequency $\omega$ is chosen to represent the circadian cycle length of 24 hours.

In an embodiment, a marker indicative of the worsening medical condition of the patient is determined when a change in at least one of mesor, amplitude and acrophase of the Cosinor analysis of TDTD occurs. In some cases, a change takes place in the amplitude of the body temperature circadian rhythm 4 weeks prior to death of the patient. In some cases, a change takes place in the amplitude of the body temperature circadian rhythm 8 weeks prior to decompensation of the patient.

Approximate entropy is a measure of irregularity in a time series data. Tempogram is a graphic technique to visualize the pattern in the circadian temperature variation. One axis is a fixed duration of time (for example, 48 hours); and the other axis is the duration for temperature data acquisition. In some cases, the hourly temperature average is compared to the daily temperature average for each day. If the hourly temperature is above the daily average a black box is assigned to that time slot, otherwise the box is left blank. In some cases, such a graph is double-plotted with day 1 and day 2 on the first line, day 2 and day 3 on the second line, and so on.

Day-night mean temperature difference is the difference in the average body temperature during the day and night cycles. Body temperature daily range is the difference in the hourly maximum and minimum body temperature. Interdaily stability (IS) is a measure of the consistency of the phase of the circadian variation in body temperature on consecutive days.

$$IS = \frac{N\sum_{h=1}^{p}(\overline{X}_h - \overline{X})^2}{p\sum_{i=1}^{N}(X_i - \overline{X})^2}$$

where N is the total number of measurements; p is the number of measurements per day, $\overline{X}$ is the mean of all measurements, $\overline{X}_h$ is the hourly means, and $X_i$ is the value for each measurement.

Time-lag embedding assumes differential equations can be used to represent a dynamic system and attempts to describe the system through creating a state space. Different embedding dimensions may be used (e.g., n=2 for simplicity). Various embedding time lags (e.g., 6, 12, 24, 36, and 48 hours) may be used based on a known cycle length of 24 hours. In an embodiment, time-lag embedding reveals a gradual spiral corresponding to circadian temperature fluctuations; the declining amplitude gives way to a "tail" region corresponding to the temperature decline observed before death. This technique corroborates the change in the amplitude of the body temperature circadian rhythm in Cosinor analysis of the TDTD for predicting the worsening of a patient's medical condition.

In other embodiments, the marker indicative of the worsening medical condition is determined when oscillation occurs in the amplitude of the peak at the patient's circadian frequency in the FDR. In an embodiment, the marker indicative of the worsening medical condition is determined when an increase occurs in the harmonics of the FDR at frequencies lower than the patient's circadian frequency compared to the patient's normal state as illustrated in FIG. 1. The circadian frequency (e.g., 1.157e-05 Hz) relates to the natural and expected circadian variation in temperature. The amplitude of the lower frequencies (e.g., 1.929e-06 Hz to 7.716e-06 Hz) relates to the slope of the decline of the patient's temperature observed prior to the worsening of his medical condition.

In certain embodiments, the outputs of at least two analysis techniques (for the TDTD, FDR, or both) are weighed to render a total score indicative of the patient's current condition. In some cases, the optimal weighing multiplication factors are determined by using Receiver Operator Characteristic (ROC) curves. The advantages of weighing the results of more than one technique include increased sensitivity, specificity, lead time, and positive predictivity compared to a single technique for tracking a patient's medical condition. Sensitivity is a statistical measure of the number of people with worsening medical condition who are correctly identified. Specificity is a statistical measure of the number of people without worsening medical condition who are correctly identified. Lead time is the length of time from prediction of worsening medical condition to the clinical presentation of symptoms associated with the worsening medical condition. Positive predictive value is the percentage of those correctly identified as having worsening medical condition. In mathematical terms, if TP is defined as the number of true positives, TN is the number of true negatives, FP is the number of false positives, and FN is the number of false negatives: Sensitivity=TP/(TP+FN); Specificity=TN/(FP+TN); Positive Predictive Value=TP/(TP+FP); Negative Predictive Value=TN/(FN+TN).

Figure 3:
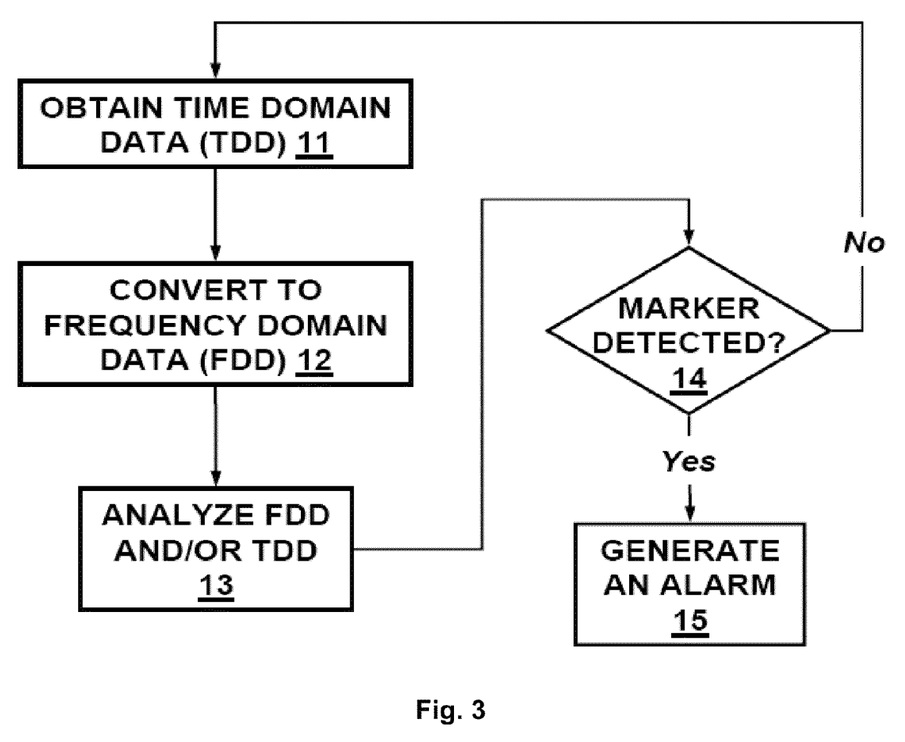
FIG. 3 illustrates a method of predicting the worsening medical condition of a patient in accordance with various embodiments.

In some embodiments, as shown in FIG. 3, after time domain data (TDD) is obtained (11), TDD is converted (12) to frequency domain data (FDD); TDD or FDD or both are analyzed (13) by a technique or a combination of at least two techniques described above to determine the marker indicative of the worsening medical condition of the patient. In some cases, if such a marker is detected (14), an alarm is generated (15) to alert the patient or a healthcare provider or both. The alarm mechanism comprises any suitable means, such as audible sounds, visual indicators, emails, automated phone calls, or pager signals sent to a healthcare provider. In some cases, if no marker is detected (14), a new series of TDD is obtained (11) to repeat steps 11-14. In some cases, TDD collection duration for each cycle of steps 11-14 is determined by the data window needed for converting the TDD to the FDD. In some other cases, TDD collection duration is predetermined and set by a healthcare provider, such as a few days, one week, 2 weeks, or 4 weeks.

In some embodiment, if a marker is detected, therapy is delivered to the patient. For example, an electrical stimulation signal is generated in the pulse generator of a pacemaker or a defibrillator implanted in the patient upon determination of the marker. Another example of therapy is the delivery of a drug to the patient either by the patient or someone else or an implanted drug reservoir with a pump that is activated to minister the drug to the patient upon detection of the marker.

In certain embodiments, whether or not a marker is detected, at least one of the TDTD, the FDR, analysis outputs, and the total score is reported to the patient or a healthcare provider or both.

System for Predicting

Figure 4:
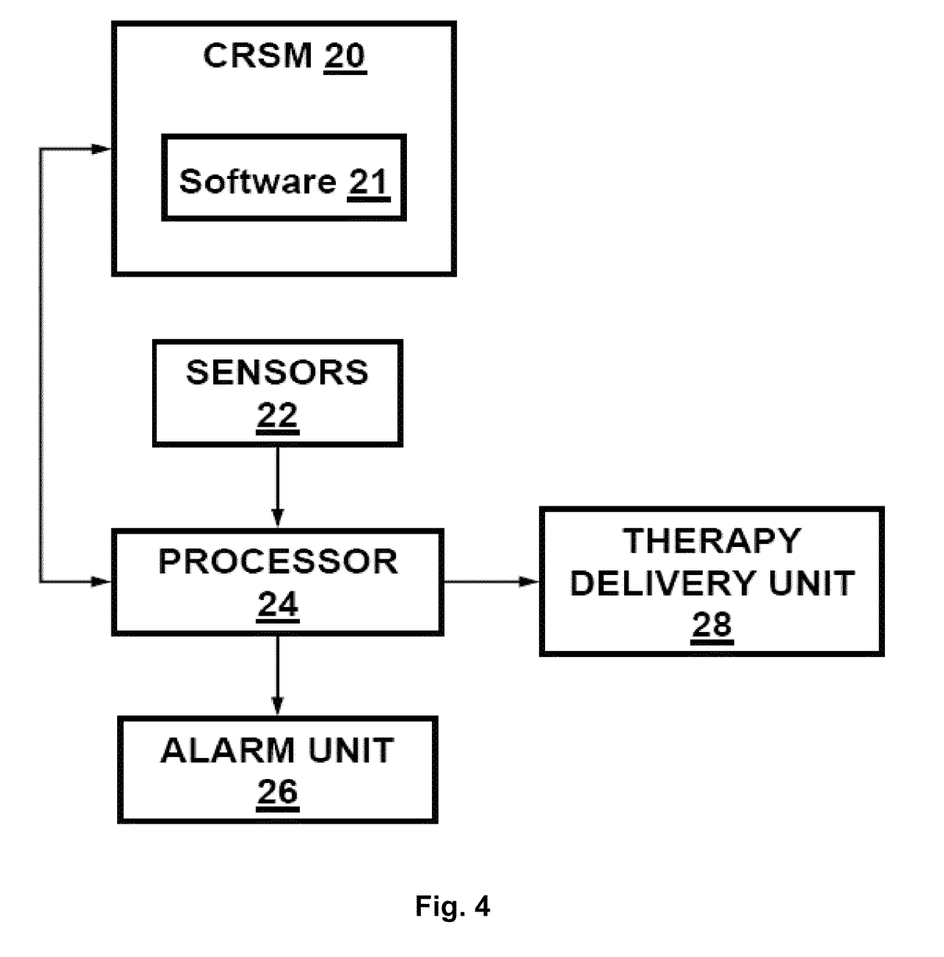
FIG. 4 illustrates a system for predicting the worsening medical condition of a patient in accordance with various embodiments.

As illustrated in FIG. 4, in some embodiments, a system to predict the worsening medical condition of a patient comprises one or more temperature sensors (22), a processor (24), an alarm unit (26), a therapy delivery unit (TDU) (28), and a computer-readable storage medium (CRSM, 20) containing software (21). Software 20, when executed by processor 24, causes the processor to receive time domain temperature data (TDTD) pertaining to a patient measured by sensors 22. Processor 24 also converts the TDTD to a frequency domain representation (FDR) and determines a marker indicative of the worsening medical condition of the patient by analyzing the FDR or by analyzing TDTD or by analyzing both. Processor 24 and CRSM 20, in coordination, also store at least one of the TDTD, FDR, analysis outputs, and the total score. The stored data are utilized according to the technique or the combination of techniques chosen to predict the worsening medical condition of the patient. The stored data may also be reported to the patient or a healthcare provider or both.

The system illustrated in FIG. 4 can be implemented in accordance with various embodiments. For example, the components depicted in FIG. 4 may all be included within a single housing. Examples of such an embodiment include pacemakers, defibrillators, and drug delivery devices. Such systems may be implantable and, as such, are powered by a power source, such as batteries, body fuel cells. The TDU 28 may comprise a pulse generator for delivering an electrical signal to, for example, the patient's heart or may comprise a drug delivery mechanism. The temperature sensor(s) 22 may be included within the same housing or may be separate from the housing, but in communication with processor 24 (wired or wireless connection). The alarm unit 26 may also be part of the same housing or provided apart from the housing but still implanted. As an implanted device, the alarm unit 26 may comprise a buzzer or other type of vibration device that the patient can feel thereby informing the patient of the worsening condition.

In other embodiments, the alarm unit 26 is external to the patient and the remaining components in FIG. 4 are implanted. The processor 24 communicates with the alarm unit 26 via a wireless, transdermal communication. The alarm unit 26 in this embodiment may generate an audible signal, a visual signal (e.g., a warning light), send an email message to the patient and/or healthcare provider, or other suitable action.

In yet other embodiments, the system of FIG. 4, except for sensor(s) 22, may be completely external to the patient. The system, for example, may comprise a bedside monitor or other type of computer system. The sensor(s) 22 may be any of the types of sensors noted above (implanted or external) and provide a signal indicative of the patient's temperature to the processor. The alarm unit 26 may comprise logic in the bedside monitor and may display an alarm (e.g., flashing indicator), generate an audible alarm on the bedside monitor, etc.

The CRSM 20 comprises volatile storage (e.g., random access memory), non-volatile storage (e.g., hard disk drive, compact disc, flash storage, read only memory, etc.), or combinations thereof.

In some cases, when a marker indicative of the patient's worsening medical condition is determined, processor 24 sends a signal to therapy delivery unit (TDU) 28 to deliver therapy to the patient. In some cases, the TDU 28 includes an implantable medical device. As an illustration, such a system comprises a pacemaker or a defibrillator including an electrical pulse generator and a processor. The processor receives the TDTD pertaining to a patient, performs Cosinor analysis on the TDTD, and determines a marker indicative of the worsening medical condition of the patient upon detecting a change in at least one of the mesor, amplitude, and acrophase of the Cosinor analysis of the TDTD. Furthermore, upon determination of the marker, processor 24 sends a signal to cause the electrical pulse generator to generate an electrical stimulation signal. Such a signal is transmitted via a suitable means. For example, the TDU 28 may receive the signal sent by the processor 24 via wired connection or wireless transmission. In some cases, the processor of such a device reports at least one of the TDTD, the FDR, analysis outputs, and the total score to the patient or a healthcare provider, or both. In some cases, such a device further comprises an alarm unit that generates an alarm upon determining the marker indicative of the worsening medical condition of the patient.

In some other cases, the TDU 28 delivers a drug to the patient when a marker indicative of the patient's worsening medical condition is determined. The TDU 28 comprises an implanted drug reservoir and an implanted pump that is connected to the reservoir. Upon determination of the marker, processor 24 sends a signal to activate the pump so that a drug contained in the reservoir is ministered to the patient. Such a signal is transmitted via a suitable means. For example, the TDU 28 may receive the signal sent by the processor 24 via wired connection or wireless transmission.

Implanted temperature sensors provide 24-hour monitoring of the patient's medical condition wherever the patient is. External temperature sensors may be applied, for example, in an Intensive Care Unit (ICU) setting, where a patient's temperature may be continuously monitored through one of many available devices, such as rectal temperature probe, Foley™ urinary catheter with a thermistor, Swan-Ganz™ thermodilution cardiac output catheter or pulmonary artery catheter. The patient may also manually measure his own temperature and report (or store or input) the temperature readings to the processor.

EXAMPLES

Various embodiments of the invention have been generally described. The following examples demonstrate the practice and advantages of the various embodiments described above. It is understood that the examples are given by way of illustration and are not intended to limit the specification of the claims to follow in any manner.

Example 1

Data Sciences International transmitters were intraperitoneally implanted into 48 male BIO-TO-2 Syrian dilated cardiomyopathic hamsters to continuously monitor their temperature until death. The body temperature was recorded every 15 minutes. The time domain temperature data (TDTD) was converted to frequency domain representation (FDR) after the changing point (the time at which the body temperature starts to decline).

As shown in FIG. 1, an increase in the low frequency component of the FDR (top panel) coincides with the decrease in temperature (bottom panel). Therefore, an increase in the low-frequency harmonics of the FDR is a marker indicative of the worsening medical condition of a patient. This method is expected to be applicable to humans.

Example 2

Data Sciences International transmitters were intraperitoneally implanted into 48 male BIO-TO-2 Syrian dilated cardiomyopathic hamsters to continuously monitor their temperature until death. Group mean Cosinor analysis was used to determine the mesor, amplitude, and acrophase of the body temperature circadian rhythm (BTCR) for both their baseline state and their state 1 month before death. FIG. 2 is the comparison of the BTCR Cosinor analysis between these two states ("Baseline" vs. "1 month before death").

45 hamsters were included in the final analysis and 44 of them showed a decline in temperature 8±4 days before death; whereas the Cosinor analysis of the temperature data showed a significant decrease in the amplitude of the BTCR 8 weeks before death compared to baseline. This example demonstrates the lead time of the disclosed method in predicting the worsening medical condition of a patient. Humans and hamsters both have established circadian body temperature rhythms; therefore the disclosed method is expected to be applicable to humans.

While embodiments of the disclosure have been shown and described, modifications thereof can be made by one skilled in the art without departing from the spirit and teachings of the disclosure. The embodiments described herein are exemplary only, and are not intended to be limiting. Many variations and modifications of the disclosure disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_L$, and an upper limit, $R_U$, is disclosed, any number falling within the range is specifically disclosed. In particular, the following numbers within the range are specifically disclosed: $R=R_L+k^*(R_U-R_L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the embodiments of the present disclosure. The discussion of a reference is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural, or other details supplementary to those set forth herein.

What is claimed is:

1. A method of predicting worsening of heart failure in a patient, comprising:
    obtaining, by a processor, time domain temperature data (TDTD) of core body temperature of the patient taken over a time period of more than one day;
    converting, by said processor, said TDTD to a frequency domain representation (FDR);
    determining, by said processor, a first marker indicative of worsening of heart failure of the patient by analyzing the FDR;
    determining, by said processor, a second marker indicative of worsening of heart failure by analyzing the TDTD, wherein analyzing the TDTD comprises performing at least one of Cosinor analysis, approximate entropy, tempogram, day-night mean temperature difference, body temperature daily range, interdaily stability, and time-lag embedding;
    weighing outputs of at least two analysis techniques to render a total score indicative of the current condition of the patient, wherein the at least two analysis techniques comprise a technique for analyzing the TDTD and another technique for analyzing the FDR; and
    determining that the patient is experiencing worsening heart failure based on the total score.

2. The method of claim 1 wherein said TDTD is selected from the group consisting of temperature taken by a Foley™ urinary catheter, temperature taken by a rectal probe, rectal cavity temperature, bladder temperature, esophagus temperature, trachea temperature.

3. The method of claim 1 wherein obtaining the TDTD comprises acquiring temperature values from at least one temperature sensor or reading temperature values from storage.

4. The method of claim 1 wherein converting said TDTD to FDR comprises performing at least one of Fourier transform, wavelet transform, and Chirplet transform.

5. A system comprising a processor that receives time domain temperature data (TDTD) pertaining to a patient, converts said TDTD to a frequency domain representation (FDR), and determines a first marker indicative of worsening of heart failure of the patient by analyzing the FDR and determines a second marker indicative of worsening of heart failure by analyzing the TDTD, wherein analyzing the TDTD comprises performing at least one of Cosinor analysis, approximate entropy, tempogram, day-night mean temperature difference, body temperature daily range, interdaily stability, and time-lag embedding, wherein the processor weighs outputs of at least two analysis techniques to render a total score indicative of the current condition of the patient, wherein the at least two analysis techniques comprise a technique for analyzing the TDTD and another technique for analyzing the FDR.

6. The system of claim 5 wherein said processor utilizes at least one of Fourier transform, wavelet transform, and Chirplet transform to convert said TDTD to FDR.

7. The system of claim 5 wherein the first marker indicative of worsening of heart failure is determined upon detecting oscillation in the amplitude of the peak at the patient's circadian frequency in the FDR.

8. The system of claim 5 wherein the first marker indicative of worsening of heart failure is determined upon detecting an increase in the harmonics of the FDR at frequencies lower than the patient's circadian frequency.

9. The system of claim 5 wherein the second marker indicative of worsening of heart failure is determined upon detecting a change in at least one of the mesor, amplitude, and acrophase of the Cosinor analysis of the TDTD.

10. The system of claim 5 wherein said processor reports at least one of the TDTD, the FDR, analysis outputs, and the total score to the patient or a healthcare provider, or both.

11. The system of claim 5 further comprising an alarm unit that generates an alarm upon the processor determining that at least one of the markers indicative of worsening of heart failure of the patient has exceeded a threshold.

12. The system of claim 5 further comprising a therapy delivery unit (TDU) that delivers therapy to the patient upon the processor determining that at least one of the markers indicative of worsening of heart failure of the patient has exceeded a threshold.

13. The system of claim 12, wherein the TDU comprises an implantable medical device.

14. The system of claim 12, wherein the TDU comprises an implantable pacemaker or defibrillator, comprising a pulse generator which is configured to generate an electrical stimulation signal upon determining that at least one of the markers has exceeded a threshold.

15. The system of claim 12, wherein the TDU comprises an implantable drug reservoir and a pump which is connected to the drug reservoir and configured to be activated upon determining that at least one of the markers has exceeded a threshold to deliver a drug in the reservoir to the patient.

16. The system of claim 5 further comprising a temperature sensor.

17. The system of claim 5 wherein the system is implantable.

18. The system of claim 5 further comprising an alarm unit that generates an alarm upon the processor determining that both the first and second markers indicative of worsening of heart failure of the patient have exceeded a threshold.

19. A non-transitory computer-readable storage medium (CRSM) containing software that, when executed by a processor, causes the processor to:
receive time domain temperature data (TDTD) of core body temperature of a patient taken over a time period of more than one day;
convert said TDTD to a frequency domain representation (FDR);
determine a first marker indicative of worsening of heart failure of the patient by analyzing the FDR;
determine a second marker indicative of worsening of heart failure by analyzing the TDTD, wherein analyzing the TDTD comprises performing at least one of Cosinor analysis, approximate entropy, tempogram, day-night mean temperature difference, body temperature daily range, interdaily stability, and time-lag embedding; and
weigh outputs of at least two analysis techniques to render a total score indicative of the current condition of the patient, wherein the at least two analysis techniques comprises a technique for analyzing the TDTD and another technique for analyzing the FDR.

20. The non-transitory CRSM of claim 19 wherein said software further causes the processor to report at least one of the TDTD, the FDR, analysis outputs, and the total score to the patient or a healthcare provider, or both.

21. The non-transitory CRSM of claim 19 wherein said software further causes the processor to activate an alarm unit connected to said processor to generate an alarm upon determining that at least one of the markers is indicative of worsening of heart failure of the patient.

22. An implantable medical device comprising
a pacemaker or a defibrillator including an electrical pulse generator; and
a processor that receives time domain temperature data (TDTD) of core body temperature of a patient taken over a time period of more than one day, performs Cosinor analysis on said TDTD, converts said TDTD to a frequency domain representation (FDR), determines a first marker indicative of worsening of heart failure of the patient upon detecting a change in at least one of the mesor, amplitude, and acrophase of the Cosinor analysis of the TDTD, and determines a second marker indicative of worsening of heart failure by analyzing the FDR;
wherein said electrical pulse generator is configured to generate an electrical stimulation signal upon determination that at least one of the markers has exceeded a threshold; and
wherein the processor computes a score based on both the TDTD and the FDR.

23. The device of claim 22 further comprising an alarm unit that generates an alarm upon determining that at least one of the markers indicative of worsening of heart failure of the patient has exceeded a threshold.

* * * * *